(12) United States Patent
Tung

(10) Patent No.: US 8,338,425 B2
(45) Date of Patent: Dec. 25, 2012

(54) HETEROCYCLIC KINASE INHIBITORS

(75) Inventor: Roger Tung, Lexington, MA (US)

(73) Assignee: Concert Pharmaceuticals, Inc., Lexington, MA (US)

(*) Notice: Subject to any disclaimer, the term of this patent is extended or adjusted under 35 U.S.C. 154(b) by 856 days.

(21) Appl. No.: 12/331,431

(22) Filed: Dec. 9, 2008

(65) Prior Publication Data

US 2009/0149399 A1 Jun. 11, 2009

Related U.S. Application Data

(60) Provisional application No. 61/012,780, filed on Dec. 10, 2007.

(51) Int. Cl.
*A61K 31/497* (2006.01)
*C07D 403/14* (2006.01)

(52) U.S. Cl. .................................. 514/252.19; 544/295
(58) Field of Classification Search ............. 514/252.19; 544/295
See application file for complete search history.

(56) References Cited

U.S. PATENT DOCUMENTS

| | | | |
|---|---|---|---|
| 6,221,335 | B1 | 4/2001 | Foster |
| 6,440,710 | B1 | 8/2002 | Keinan et al. |
| 6,603,008 | B1 * | 8/2003 | Ando et al. ............... 546/269.7 |
| 7,189,854 | B2 | 3/2007 | Das et al. |
| 7,517,990 | B2 | 4/2009 | Ito et al. |
| 2006/0235006 | A1 | 10/2006 | Lee et al. |
| 2007/0082929 | A1 | 4/2007 | Gant et al. |
| 2007/0197695 | A1 * | 8/2007 | Potyen et al. ............... 524/110 |
| 2009/0076025 | A1 * | 3/2009 | Czarnik .................... 514/252.19 |

FOREIGN PATENT DOCUMENTS

WO WO-95/26325 10/1995
WO WO-2006/099474 9/2006

OTHER PUBLICATIONS

Foster, A.B., "Deuterium isotope effects in studies of drug metabolism", TIPS 524-527 (Dec. 1984).
Gouyette, A., Biomedical and Environmental Mass Spectrometry, vol. 15, 243-247 (1988).
Cherrah, Y. et al., Biomedical and Environmental Mass Spectrometry, vol. 14, Issue 11, pp. 653-657 (1987).
Dyck, L.E. et al., Journal of Neurochemistry, vol. 46, Issue 2, pp. 399-404 (1986).
Tonn, G.R., et al., Biological Mass Spectrometry, vol. 22, Issue 11, pp. 633-642 (1993).
Haskins, N.J., Biomedical Spectrometry, vol. 9, Issue 7, pp. 269-277 (1982).
Wolen, R.L., J. Clin. Pharmacology 26: 419-424 (1986).
Pieniaszek, H.J. et al., J. Clin. Pharmacol. 39:817-825 (1999).
Honma, S. et al., Drug Metab Dispos 15(4): 551-559 (1987).
Browne, T.R., Journal of Clinical Pharmacology 38: 213-220 (1998).
Baillie, T.A., Pharmacology Rev. 33:81-132 (1981).
Foster, A.B., Adv Drug Res, 14:1-40 (1985).
Fisher et al., The complexities inherent in attempts to decrease drug clearance by blocking sites of CYP-mediated metabolism. Curr Opin Drug Discov Devel. 9(1): 101-9 (2006).
Kushner, et al., "Pharmacological uses and perspectives of heavy water and deuterated compounds", Can. J. Physiol. Pharmacol. 77: 79-88 (1999).
Christopher et al., "Metabolism and Disposition of Dasatinib after Oral Administration to Humans", Drug Metabolism and Disposition, vol. 36, No. 7, pp. 1357-1364 (2008).
Christopher et al., "Biotransformation of [$^{14}$C]Dasatinib: In Vitro Studies in Rat, Monkey, and Human and Disposition after Administration to Rats and Monkeys", Drug Metabolism and Disposition, vol. 36, No. 7, pp. 1341-1356 (2008).
Sprycel ® (dasatinib) Tablet for Oral Use, Highlights of Prescribing Information (Revised Jun. 2009).
The International Search Report and Written Opinion mailed Jan. 26, 2009 in corresponding PCT Application No. PCT/US08/86108.
The Supplemental European Search Report dated Nov. 4, 2010, in corresponding European Patent Application No. 08859849.5.
Li et al., "Characterization of Dasatinib and Its Structural Analogs as CYP3A4 Mechanism-Based Inactivators and the Proposed Bioactivation Pathways", Drug Metabolism and Disposition, vol. 37, No. 6, pp. 1242-1250 (2009).
Das et al., "2-Aminothiazole as a Novel Kinase Inhibitor Template. Structure-Activity Relationship Studies toward the Discovery of *N*-(2-Chloro-6-methylphenyl)-2-[[6-[4-(2-hydroxyethyl)-1-piperazinyl)]-2-methyl-4-pyrimidinyl]amino)]-1,3-thiazole-5-carboxamide (Dasatinib, BMS-354825) as a Potent *pan*-Src Kinase Inhibitor", *J. Med. Chem.*. 49, 6819-6832 (2006).

* cited by examiner

*Primary Examiner* — James O Wilson
*Assistant Examiner* — Ebenezer O Sackey
(74) *Attorney, Agent, or Firm* — Edwards Wildman Palmer LLP; Jeffrey D. Hsi; Mark D. Russett

(57) ABSTRACT

This invention relates to novel 2-{6-[4-(2-hydroxy-ethyl)-piperazin-1-yl]-2-methyl-pyrimidin-4-ylamino}-thiazole-5-carboxylic acid (2-chloro-6-methyl-phenyl)-amide derivatives, and pharmaceutically acceptable acid addition salts thereof. The invention also provides compositions comprising a compound of this invention and the use of such compositions in methods of treating diseases and conditions beneficially treated by the inhibition of kinases including Src-kinase and Bcr-Abl kinase.

4 Claims, 1 Drawing Sheet

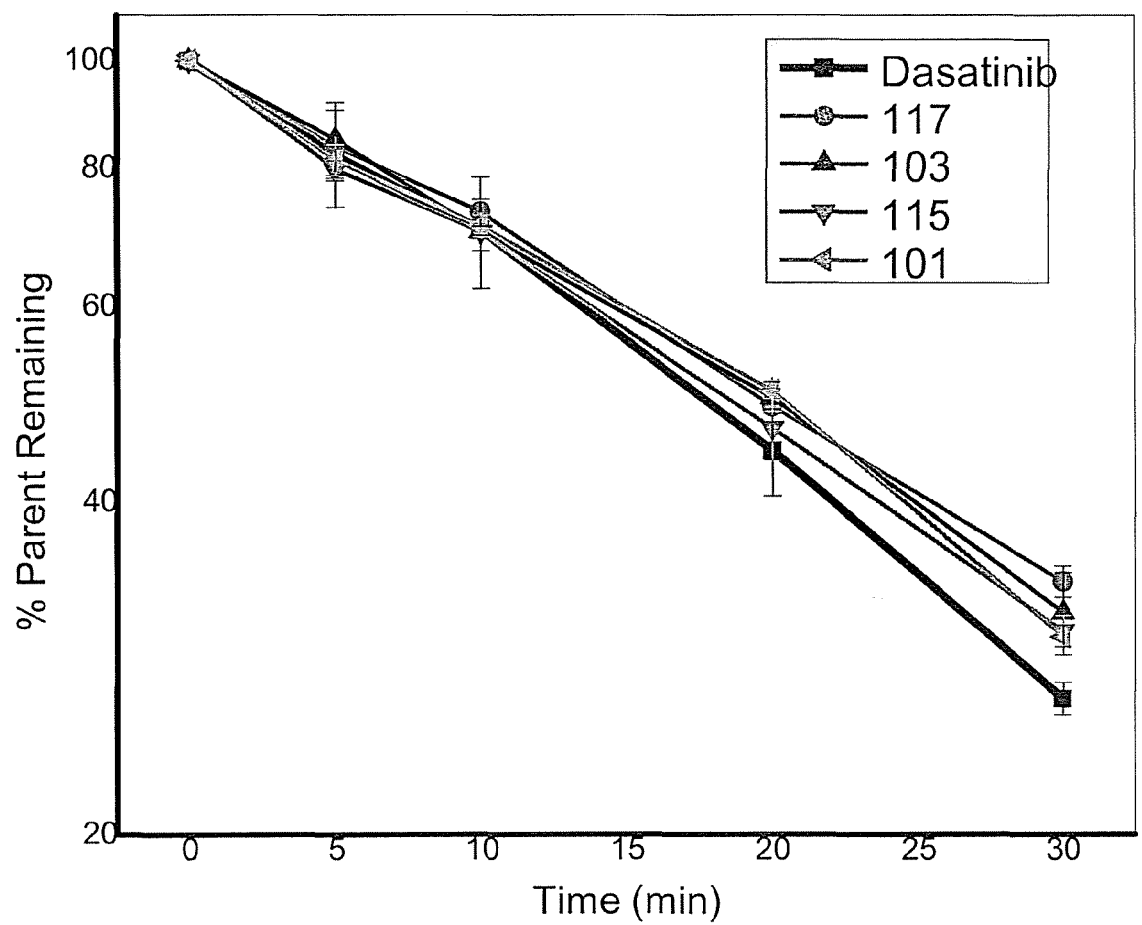

HETEROCYCLIC KINASE INHIBITORS

RELATED APPLICATIONS

This application claims the benefit of U.S. Provisional Application Ser. No. 61/012,780, filed Dec. 10, 2007, which is incorporated by reference herein in its entirety.

BACKGROUND

This invention relates to novel 2-{6-[4-(2-hydroxy-ethyl)-piperazin-1-yl]-2-methyl-pyrimidin-4-ylamino}-thiazole-5-carboxylic acid (2-chloro-6-methyl-phenyl)-amide derivatives, and pharmaceutically acceptable acid addition salts thereof. The invention also provides compositions comprising a compound of this invention and the use of such compositions in methods of treating diseases and conditions beneficially treated by the inhibition of kinases including Src-kinase and Bcr-Abl kinase.

The kinase inhibitor, 2-{6-[4-(2-Hydroxy-ethyl)-piperazin-1-yl]-2-methyl-pyrimidin-4-ylamino}-thiazole-5-carboxylic acid (2-chloro-6-methyl-phenyl)-amide, is disclosed in U.S. Pat. No. 7,125,875 and U.S. Pat. No. 6,596,746, and is identified as dasatinib.

This inhibitor of Src-kinase and Bcr-Abl kinase is used to treat chronic myelogenous leukemia and Philadelphia chromosome-positive acute lymphoblastic leukemia and has been studied or is currently in 37 clinical trials (see ClincalTrials.gov website for Sprycel®). In addition to the approved indications, dasatinib is also in trials for refractory solid tumors, breast cancer, prostate cancer, myeloproliferative disorders, and chronic lymphocytic leukemia.

Dasatinib is extensively metabolized in humans, primarily by CYP 3A4. A number of these metabolites are disclosed in WO 2006/099474 and also reported for treatment of cancer, although no kinase inhibitory activity is disclosed for the compounds.

Despite the beneficial uses of dasatanib, a need remains for new and improved agents to treat cancer.

DEFINITIONS

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of dasatinib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert", "$^t$", and "t-" each refer to tertiary. "US" refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

LIST OF FIGURES

FIG. 1 depicts the HLM stability of compounds 117 and 103 as compared to Dasatinib.

THERAPEUTIC COMPOUNDS

The present invention provides a compound of Formula I

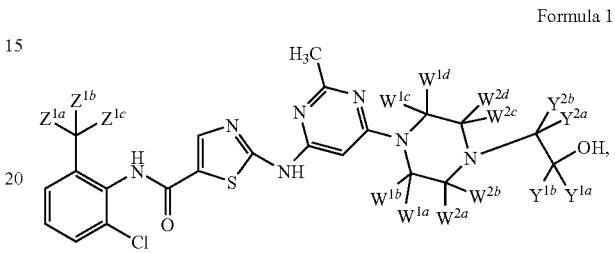

Formula 1 or a pharmaceutically acceptable salt thereof; wherein:
each W is independently selected from hydrogen or deuterium;
each Y is independently selected from hydrogen or deuterium;
each Z is independently selected from hydrogen or deuterium; and
at least one W, Y, or Z is deuterium.

In one embodiment, the invention provides a compound of the invention wherein $Y^{1a}$ and $Y^{1b}$ are the same. In a more specific embodiment, $Y^{1a}$ and $Y^{1b}$ are simultaneously deuterium.

In another embodiment, the invention provides a compound of the invention wherein $Y^{2a}$ and $Y^{2b}$ are the same. In a more specific embodiment, $Y^{2a}$ and $Y^{2b}$ are simultaneously deuterium.

In still another embodiment, the invention provides a compound of the invention wherein $Z^{1a}$, $Z^{1b}$, and $Z^{1c}$ are the same. In a more specific embodiment, $Z^{1a}$, $Z^{1b}$, and $Z^{1c}$ are simultaneously deuterium.

In certain embodiments, the invention provides a compound of the invention wherein $W^{1a}$, $W^{1b}$, $W^{1c}$ and $W^{1d}$ are the same. In a more specific embodiment, $W^{1a}$, $W^{1b}$, $W^{1c}$ and $W^{1d}$ are simultaneously deuterium. In certain aspects of these embodiments, $Z^{1a}$, $Z^{1b}$, and $Z^{1c}$ are also simultaneously deuterium.

In other embodiments, the invention provides a compound of the invention wherein $W^{2a}$, $W^{2b}$, $W^{2c}$ and $W^{2d}$ are the same. In a more specific embodiment, $W^{2a}$, $W^{2b}$, $W^{2c}$ and $W^{2d}$ are simultaneously deuterium. In certain aspects of these embodiments, $Z^{1a}$, $Z^{1b}$, and $Z^{1c}$ are also simultaneously deuterium.

Specific compounds of Formula (I) are shown in Table 1.

TABLE 1

| Cmpd | Each $Y^1$ | Each $Y^2$ | Each Z | Each $W^1$ | Each $W^2$ |
|------|-----------|-----------|--------|-----------|-----------|
| 100  | D         | D         | H      | H         | H         |
| 101  | D         | H         | D      | H         | H         |
| 102  | H         | D         | D      | H         | H         |
| 103  | D         | D         | D      | H         | H         |
| 104  | D         | D         | H      | D         | H         |
| 105  | D         | D         | H      | H         | D         |

TABLE 1-continued

| Cmpd | Each Y¹ | Each Y² | Each Z | Each W¹ | Each W² |
|---|---|---|---|---|---|
| 106 | D | H | D | D | H |
| 107 | D | H | D | H | D |
| 108 | H | D | D | D | H |
| 109 | H | D | D | H | D |
| 110 | D | D | D | D | H |
| 111 | D | D | D | H | D |
| 112 | D | D | H | D | D |
| 113 | D | H | D | D | D |
| 114 | H | D | D | D | D |
| 115 | D | D | D | D | D |
| 116 | D | H | H | H | H |
| 111 | H | H | H | D | D |
| 118 | H | H | D | H | H |
| 119 | H | H | D | D | D |

In another set of embodiments, any atom not designated as deuterium in any of the embodiments set forth above is present at its natural isotopic abundance.

The synthesis of compounds of the formulae herein can be readily effected by synthetic chemists of ordinary skill. Relevant procedures and intermediates are disclosed, for instance, in U.S. Pat. No. 6,596,746; U.S. Pat. No. 7,125,875; US 2006/004067; US 2005/215795; and US 2005/176,965. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for producing compounds of the formulae herein is found in Schemes A-C, below. In the Schemes, the asterisks (*) denote sites of optional deuteration.

Scheme A shows one route for preparing compounds of Formula I. One skilled in the art would appreciate that an alternative sequence of steps may also be employed. For example, compound 10 may be coupled with 11 either before (X=H) or after (X=Cl) introduction of the halogen X. Likewise, the thiourea compounds 11 may be prepared, prior to the cyclization, having desired groups corresponding to the groups on the desired final product, or alternatively, the desired groups may be attached to the amino-thiazolyl after cyclization. All such alternative embodiments and variations thereof are contemplated as within the scope of the present invention.

The group PG in 10 may be selected from alkyl, $—SO_2OR^{10}$, $—SO_2R^{10}$, $—C(O)R^{11}$ and $—Si(R^{12})_3$, but preferably PG is an alkyl, more preferably a lower alkyl, i.e., methyl, ethyl, n-propyl, isopropyl, or a straight or branched butyl. $R^{10}$ is alkyl, substituted alkyl, aryl or heteroaryl. $R^{11}$ is alkyl, substituted alkyl, aryl or heteroaryl. $R^{12}$ is alkyl, substituted alkyl, aryl. Intermediate 10 can be prepared upon reaction of the corresponding anilines, $NHR^2Ar$, with alkoxy-acryloyl compounds. $R^2$ is preferably H or alkyl. Ar is aryl, preferably an appropriately substituted phenyl. Methods for making β-ethoxy acryl benzamides are also described, for example, in Ashwell, M A et al., J Bioorg Med Chem Lett, 2001, 24: 3123; and Yoshizaki, S et al., Chem Pharm Bull, 1980, 28: 3441.

The halogenating agent(s) may be any agent or agents as defined herein capable of halogenating compound 10, and include, but are not limited to, NCS and the N-halohydantoins. Thiourea compounds 11 include unsubstituted thioureas, N-monosubstituted thioureas, and N,N-disubstituted thioureas. The steps of halogenation and cyclization are carried out in a suitable solvent which may include one or more solvents such as hydrocarbons, ethers, esters, amides and ketones with ethers, with dioxane preferred.

SCHEME A

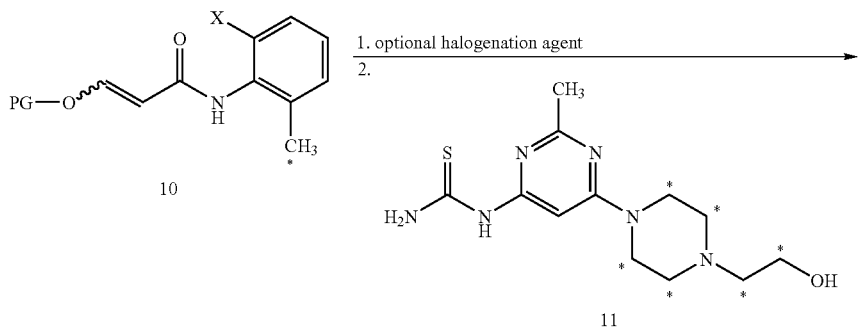

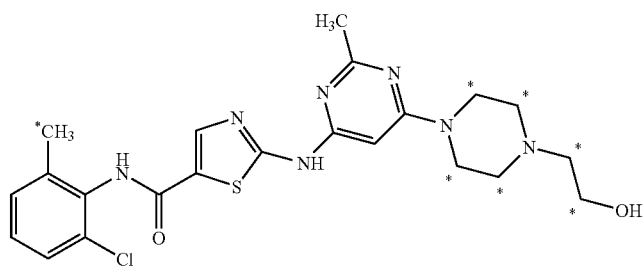

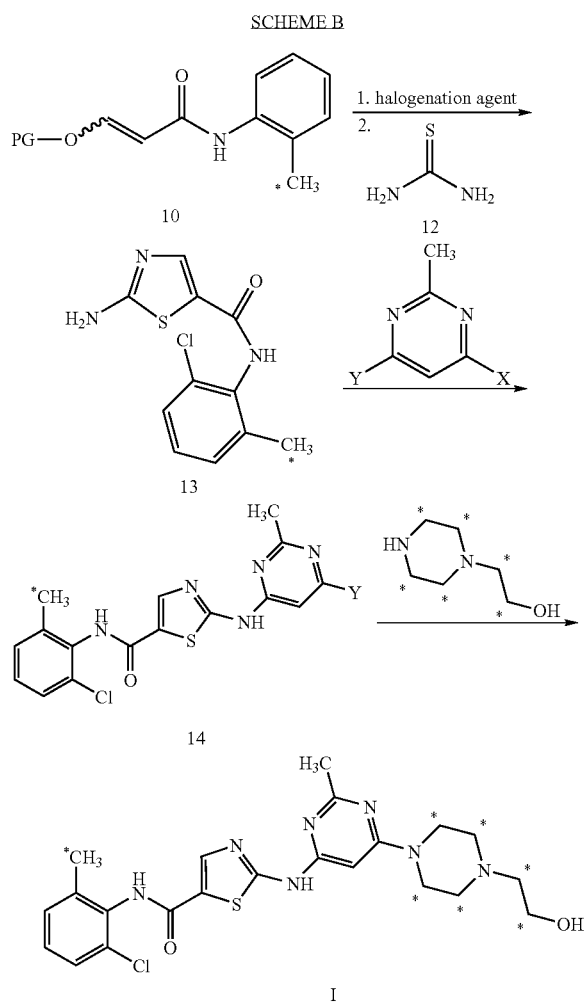

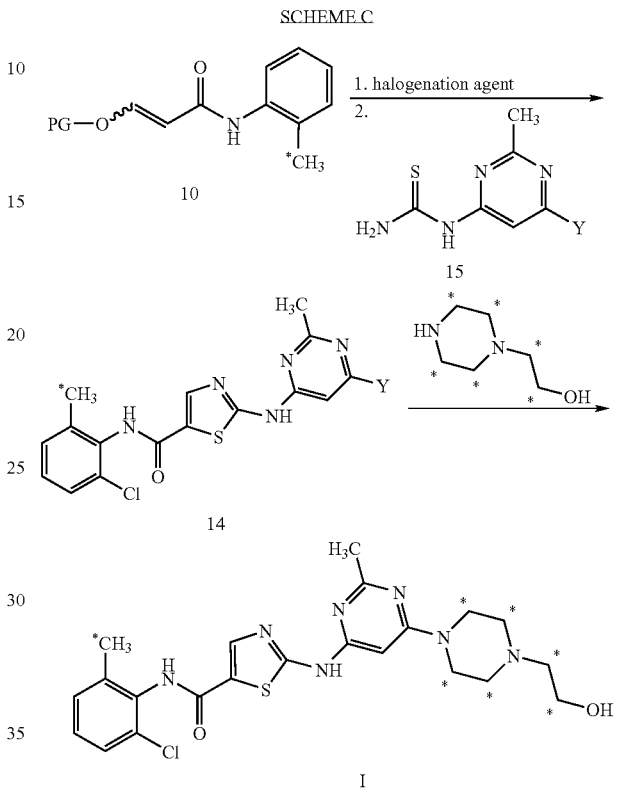

Scheme B shows an alternative route to the present compounds. Compound 10 is halogenated with a halogenating agent, such as NCS, in a suitable solvent, in the presence of water, then cyclized with unsubstituted thiourea 12. The resulting 2-(unsubstituted)amino-thiazole-5-aromatic amide 13 is reacted with a pyrimidine compound comprising X and Y (both leaving groups) to produce compounds 14. Leaving groups X and Y are preferably I, Br, Cl, or $R^{10}SO_2O$— (wherein $R^{10}$ is alkyl, substituted alkyl, aryl, or heteroaryl, as defined herein), more preferably X and Y are selected from I, Br, Cl, methyl sulfate, mesylate, trifluoromethane sulfonate, and tosylate, even more preferably from Cl and Br. Advantageously, this step is carried out in the presence of a base, wherein the bases may include alkali hydride and alkoxides with the latter such as sodium t-butoxide preferred. Suitable solvent(s) include solvents such as hydrocarbons, ethers, esters, amides, ketones and alcohols, or mixtures of the above solvents, with ethers such as THF are preferred.

Compound 14 can then be treated with a deuterated or nondeuterated cyclic amine, to provide compounds of Formula I. Advantageously, this step is carried out in the presence of a base, including inorganic and organic bases, with organic bases such as tertiary amines preferred. Suitable solvent(s) include solvents such as hydrocarbons, halogenated hydrocarbons, ethers, esters, amides, ketones, lactams and alcohols, and mixtures of the above solvents, with alcohols such as n-butanol as one non-limiting example, and DMF (dimethylformamide), DMA (dimethylacetamide) and NMP (N-methylpyrrolidine) as other examples. The compounds of Formula I thus formed may optionally be further elaborated as desired and/or purified and crystallized.

Another approach to the present compounds is shown in Scheme C. Compound 10 is treated with a halogenating agent, then further reacted with a monosubstituted thiourea 15 having attached thereto a functional pyrimidine group, wherein Y is as in Scheme B, to provide intermediate 2-substituted-aminothiazole-aromatic amides of formula 14. The compounds of formula 14 may optionally then be reacted with deuterated or nondeuterated cyclic amines to provide compounds of Formula I, and/or optionally further elaborated as desired, and/or purified and crystallized.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive*

*Organic Transformations*, VCH Publishers (1989); Greene T W et al., *Protective Groups in Organic Synthesis*, 3rd Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I (e.g., including any of the formulae herein), or a pharmaceutically acceptable salt thereof; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as dasatinib. Such agents include those indicated as being useful in combination with dasatinib, including but not limited to, those described in U.S. Pat. No. 7,125,875, U.S. Pat. No. 6,596,746, and US2005/0009891.

Preferably, the second therapeutic agent is an agent useful in the treatment or prevention of a disease or condition selected from transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; chronic obstructive pulmonary disease (COPD), such as emphysema; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituitarism; Guillain-Barre syndrome; other autoimmune diseases; cancers, including cancers where Lck or other Src-family kinases such as Src are activated or overexpressed, such as colon carcinoma and thymoma, and cancers where Src-family kinase activity facilitates tumor growth or survival; glomerulonephritis; serum sickness; urticaria; allergic diseases such as respiratory allergies (asthma, hayfever, allergic rhinitis) or skin allergies;

scleroderma; mycosis fungoides; acute inflammatory responses (such as acute respiratory distress syndrome and ischemia/reperfusion injury); dermatomyositis; alopecia greata; chronic actinic dermatitis; eczema; Behcet's disease; Pustulosis palmoplantaris; Pyoderma gangrenosum; Sezary's syndrome; atopic dermatitis; systemic sclerosis; and morphea.

Such second therapeutic agents include cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT-3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, anti-cancer agents, TNF-α inhibitors such as tenidap, anti-TNF antibodies or soluble TNF receptor such as etanercept (Enbrel), rapamycin (sirolimus or Rapamune), leflunomide (Arava), and cyclooxygenase-2 (COX-2) inhibitors such as celecoxib (Celebrex) and rofecoxib (Vioxx), or derivatives thereof, and the PTK inhibitors disclosed in U.S. Pat. Nos. 6,635,626, 6,235,740, and 5,990,109.

In one embodiment, the second therapeutic agent is selected from cetuximab, imatinib, ketoconazole, erlotinib, lenalidomide, lenalidomide and desamethasone, capecitabine, gemcitabine, bortezomib, docetaxel, valproic acid, MK0457, FOLFOX (5-FU, leucovorin and oxaliplatin), and hyper-CVAD (cyclophosphamide, vincristine, adriamycin, and dexamethasone).

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.001 mg/kg to about 500 mg/kg, more preferably 0.01 mg/kg to about 100 mg/kg, more preferably 0.1 mg/kg to about 100 mg/kg. The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day.

When administered intravenously, the compounds of the present invention are preferably administered using the formulations of the invention. Generally, the compounds of the present invention are administered by IV infusion over a period of from about 10 minutes to about 3 hours, preferably about 30 minutes to about 2 hours, more preferably about 45 minutes to 90 minutes, and most preferably about 1 hour. Typically, the compounds are administered intravenously in a dose of from about 0.5 mg/m$^2$ to 65 mg/m$^2$, preferably about 1 mg/m$^2$ to 50 mg/m$^2$, more preferably about 2.5 mg/m$^2$ to 30 mg/m$^2$, and most preferably about 25 mg/m$^2$. One of ordinary skill in the art would readily know how to convert doses from mg/kg to mg/m$^2$ given either or both the height and or weight of the patient (See, e.g., http://www.fda.gov/cder/cancer/animalframe.htm).

As discussed above, compounds of the present invention can be administered orally, intravenously, or both. In particular, the methods of the invention encompass dosing protocols such as once a day for 2 to 10 days, preferably every 3 to 9 days, more preferably every 4 to 8 days and most preferably every 5 days. In one embodiment there is a period of 3 days to 5 weeks, preferably 4 days to 4 weeks, more preferably 5 days to 3 weeks, and most preferably 1 week to 2 weeks, in between cycles where there is no treatment. In another embodiment the compounds of the present invention can be administered orally, intravenously, or both, once a day for 3 days, with a period of preferably 1 week to 3 weeks in between cycles where there is no treatment. In yet another embodiment the compounds of the present invention can be administered orally, intravenously, or both, once a day for 5 days, with a period of preferably 1 week to 3 weeks in between cycles where there is no treatment.

In one embodiment the treatment cycle for administration of the compounds of the present invention is once daily for 5 consecutive days and the period between treatment cycles is from 2 to 10 days, preferably one week. In one embodiment, a compound of the present invention is administered once daily for 5 consecutive days, followed by 2 days when there is no treatment.

The compounds of the present invention can also be administered orally, intravenously, or both once every 1 to 10 weeks, preferably every 2 to 8 weeks, more preferably every 3 to 6 weeks, and even more preferably every 3 weeks.

In another method of the invention, the compounds of the present invention are administered in a 28 day cycle wherein the compounds are intravenously administered on days 1, 7, and 14 and orally administered on day 21. Alternatively, the compounds of the present invention are administered in a 28 day cycle wherein the compound is orally administered on day 1 and intravenously administered on days 7, 14, and 28.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for dasatinib.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method reducing or inhibiting protein tyrosine kinase activity in a cell, comprising contacting a cell with one or more compounds of Formula I herein.

According to another embodiment, the invention provides a method of treating a patient suffering from, or susceptible to, a disease that is beneficially treated by dasatinib comprising the step of administering to said patient an effective amount of a compound or a composition of this invention. Such diseases are well known in the art and are disclosed in, but not limited to the following patents and published applications: U.S. Pat. No. 6,596,746; U.S. Pat. No. 7,125,875; and US 2005/009891.

In one particular embodiment, the method of this invention is used to treat a patient suffering from or susceptible to a disease or condition selected from transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; chronic obstructive pulmonary disease (COPD), such as emphysema; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituitarism; Guillain-Barre syndrome; other autoimmune diseases; cancers, including cancers where Lck or other Src-family kinases such as Src are activated or overexpressed, such as colon carcinoma and thymoma, and cancers where Src-family kinase activity facilitates tumor growth or survival; glomerulonephritis; serum sickness; urticaria; allergic diseases such as respiratory allergies (asthma, hayfever, allergic rhinitis) or skin allergies; scleroderma; mycosis fungoides; acute inflammatory responses (such as acute respiratory distress syndrome and ischemia/reperfusion injury); dermatomyositis; alopecia greata; chronic actinic dermatitis; eczema; Behcet's disease; Pustulosis palmoplantaris; Pyoderma gangrenosum; Sezary's syndrome; atopic dermatitis; systemic sclerosis; and morphea.

Specific cancers that may be treated by the methods of this invention include leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

In one embodiment, the cancer to be treated by the methods of this invention is selected from non-small-cell lung carcinoma, advanced solid malignancies, chronic lymphocytic leukemia, chronic myeloid leukemia, breast cancer, non-hodgkin's lymphoma, prostate cancer, head and neck squamous cell carcinoma, acute myeloid leukemia, myelodysplastic syndromes, agnogenic myeloid metaplasia, myelofibrosis, hypereosinophilic syndrome, polycythemia vera, mastocytosis, chronic myelomonocytic leukemia, multiple myeloma, pancreatic cancer, liver cancer, acute lymphoblastic leukemia, advanced sarcomas, acute lymphoblastic leukemia, glioblastoma multiforme, gliosarcoma, malignant mesothelioma, melanoma, colorectal cancer, small cell lung cancer, and squamous cell skin cancer.

The compounds of the present invention are also useful in the treatment of cancers that are sensitive to and resistant to chemotherapeutic agents that target BCR-ABL and c-KIT, such as, for example, Gleevec™ (STI-571).

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with dasatinib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I and a second therapeutic agent for treatment of the following conditions (with the particular second therapeutic agent indicated in parentheses following the indication): acute lymphocytic leukemia (hyper-CVAD); breast cancer (capecitabine); chronic myeloid leukemia (imatinib); colorectal cancer (FOLFOX); multiple myeloma (lenalidomide, dexamethasone, bortezomib); non-small cell lung cancer (erlotinib); prostate cancer (docetaxel); solid tumors (cetuximab, gemcitabine, valproic acid).

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

Diagnostic Methods and Kits

The present invention also provides kits for use to treat non-small-cell lung carcinoma, advanced solid malignancies, chronic lymphocytic leukemia, chronic myeloid leukemia, breast cancer, non-hodgkin's lymphoma, prostate cancer, head and neck squamous cell carcinoma, acute myeloid leukemia, myelodysplastic syndromes, agnogenic myeloid metaplasia, myelofibrosis, hypereosinophilic syndrome, polycythemia vera, mastocytosis, chronic myelomonocytic leukemia, multiple myeloma, pancreatic cancer, liver cancer, acute lymphoblastic leukemia, advanced sarcomas, acute lymphoblastic leukemia, glioblastoma multiforme, gliosarcoma, malignant mesothelioma, melanoma, colorectal cancer, small cell lung cancer, and squamous cell skin cancer. These kits comprise (a) a pharmaceutical composition comprising a compound of Formula I or a salt thereof, wherein said pharmaceutical composition is in a container; and (b) instructions describing a method of using the pharmaceutical composition to treat the appropriate cancer.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of 2-Chloro-6-(methyl-$d_3$)-aniline (41-$d_3$)

Intermediate 41-$d_3$ was prepared as outlined in Scheme 1 below. Details of the synthesis are set forth below.

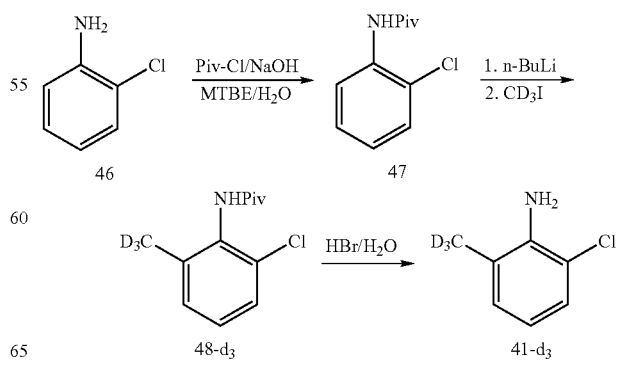

Scheme 1. Preparation of Intermediate 41-$d_3$.

Synthesis of N-(2-chlorophenyl)pivalamide (47). To a solution of 2-chloroaniline 46 (200 mL, 1.9 mol) in MTBE (950 mL) in an ice-water bath was added 25 wt % NaOH (480 g, 3 mol). Trimethylacetyl chloride (248.5 mL, 2.02 mol) was then added dropwise and the reaction was stirred overnight at rt. The organic layer was separated, washed with brine (1.0 L) and water (1.0 L), dried over sodium sulfate, and concentrated in vacuo to give 47 (390 g, 97%) as a white solid.

Synthesis of N-(2-chloro-6-(methyl-$d_3$)-phenyl)pivalamide (48-$d_3$). To a solution of pivalamide 47 (113.7 g, 536.7 mmol) and TMEDA (61.2 mL, 405.6 mmol) in anhydrous MTBE (1.08 L) at −23° C. was added dropwise 2.5 M n-BuLi (537.0 mL, 1.34 mol) at a rate allowing the internal temperature to be maintained at −23° C. Stirring at −23° C. was continued for 1.5 h followed by the addition of iodomethane-$d_3$ (77.8 g, 536.7 mmol). The reaction mixture was then stirred 1 h at rt and slowly quenched by the addition of water (500 mL). The aqueous layer was separated and extracted MTBE (2×300 mL). The combined organic layers were dried over sodium sulfate and concentrated in vacuo to give a tan solid that was triturated with 1:1 MTBE/heptane (300 mL) to give 48-$d_3$ (82.5 g, 67%) as a white solid.

Synthesis of 2-chloro-6-(methyl-$d_3$)-aniline (41-$d_3$). A suspension of 48-$d_3$ (110.8 g) in 48% hydrobromic acid (650 mL) was stirred at reflux for 24 h then concentrated to dryness. The remaining solid was dissolved in water (500 mL), brought to pH 8 with solid potassium carbonate, and extracted with MTBE (3×400 mL). The combined organic layers were dried over sodium sulfate and concentrated in vacuo to give 41-$d_3$ (70 g, 97%) as a tan oil.

Example 2

Synthesis of 2-(6-Chloro-2-methylpyrimidin-4-ylamino)-N-(2-chloro-6-(methyl-$d_3$)phenyl)thiazole-5-carboxamide (44-$d_3$)

Intermediate 44-$d_3$ was prepared as outlined in Scheme 2 below and as described below.

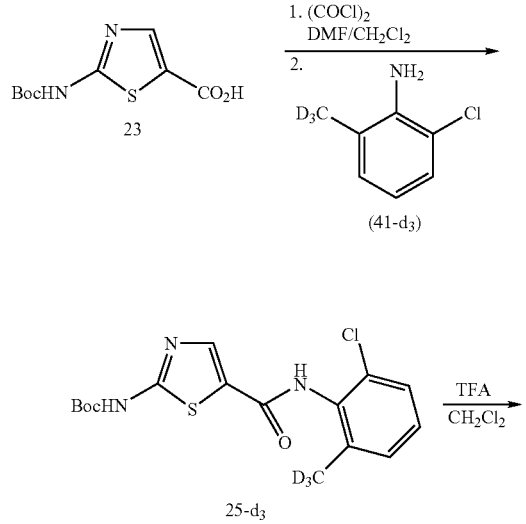

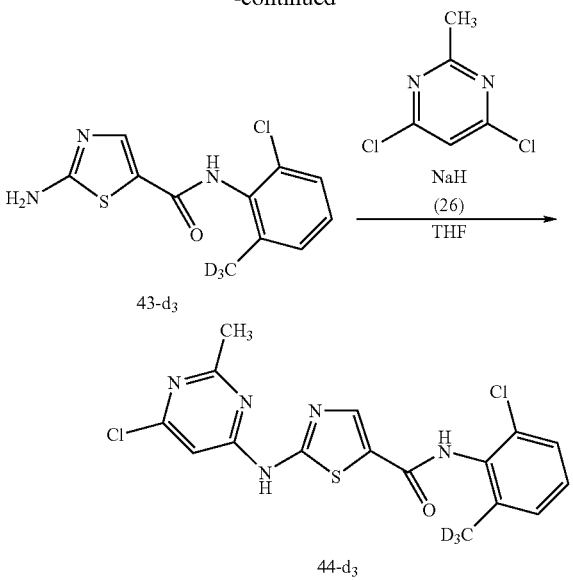

Synthesis of tert-butyl 5-(2-chloro-6-(methyl-$d_3$)phenylcarbamoyl)thiazol-2-ylcarbamate (25-$d_3$). To a suspension of 23 (46.8 g, 191.7 mmol) and N,N-dimethylformamide (0.8 mL) in $CH_2Cl_2$ (1.1 L) at 0° C. was added dropwise oxalyl chloride (24.3 mL, 287.6 mmol). The resulting reaction mixture was stirred 2 h at rt, evaporated to dryness, dissolved in $CH_2Cl_2$ (1.1 L), then cooled to 0° C. To this reaction mixture was added 41-$d_3$ (69.3 g, 479.2 mmol). After 20 minutes (min) of stirring at 0° C., diisopropylethylamine (120.0 mL, 690.1 mmol) was added and the reaction mixture was stirred 4 h at 0° C. Volatile components were removed in vacuo, and the resulting solid was dispersed in saturated sodium bicarbonate (500 mL) then was allowed to stand for 2 h. The precipitate was filtered, washed sequentially with water (300 mL) and MTBE (400 mL), and dried under vacuum at 50° C. to give 25-$d_3$ as a yellow solid (22.6 g, 32%).

Synthesis of 2-amino-N-(2-chloro-6-(methyl-$d_3$)phenyl)thiazole-5-carboxamide (43-$d_3$). To a solution of 25-$d_3$ (22.6 g, 60.9 mmol) in $CH_2Cl_2$ (100 mL) at 0° C. was added trifluoroacetic acid (200 mL). The reaction mixture was stirred 3 h at 0° C. and 1 h at rt, concentrated in vacuo, dissolved in water (200 mL), then brought to pH 8 with solid potassium carbonate, and extracted with ethyl acetate (3×300 mL). The combined organic layers were dried over sodium sulfate and concentrated in vacuo to give 43-$d_3$ as a tan foam in quantitative yield (16.5 g).

Synthesis of 2-(6-chloro-2-methylpyrimidin-4-ylamino)-N-(2-chloro-6-(methyl-$d_3$)phenyl)thiazole-5-carboxamide (44-$d_3$). To a solution of 43-$d_3$ (16.5 g, 60.9 mmol) and 4,6-dichloro-2-methylpyrimidine (10.9 g, 67.0 mmol) in anhydrous THF (530 mL) at 0° C. was added sodium hydride (9.8 g, 60 wt % in mineral oil, 243.6 mmol) in portions. The resulting mixture was stirred 2 h at rt, cooled to 0° C., and slowly quenched with saturated ammonium chloride (200 mL). The precipitate was collected by suction filtration and washed with water and MTBE sequentially to give the first batch of 44-$d_3$ as an off-white solid. The filtrate was extracted with ethyl acetate (3×300 mL) and the combined organic layers were dried over sodium sulfate, then rid of solvent in vacuo to give a crude solid that was triturated with MTBE to give the second batch of 44-$d_3$. The two batches were combined to give 44-$d_3$ (12.0 g) in 50% yield.

Example 3a

Synthesis of 1-(1,1,2,2-$d_4$-2-Hydroxyethyl)piperazine dihydrochloride (45-$d_4$)

Intermediate 45-$d_4$ was prepared as outlined in Scheme 3a below. Details of the synthesis are as follows.

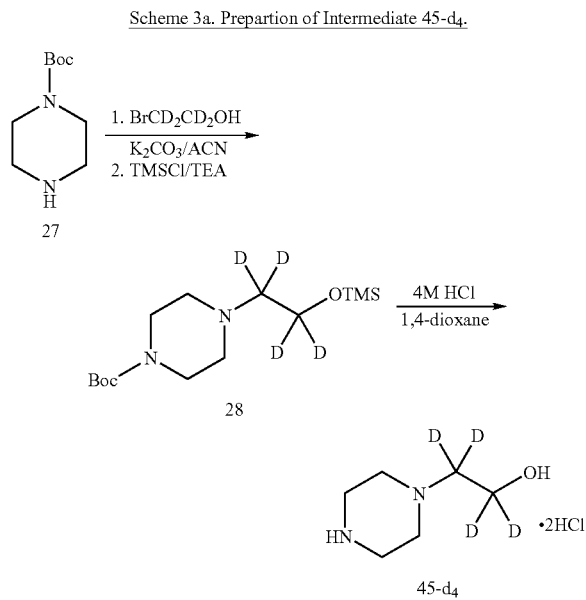

Scheme 3a. Prepartion of Intermediate 45-$d_4$.

Synthesis of tert-butyl 4-(2-(trimethylsilyloxy)-1,1,2,2-$d_4$-ethyl)piperazine-1-carboxylate (28). To a solution of 1-Boc-piperazine 27 (14.44 g, 77.6 mmol) in anhydrous acetonitrile (120 mL) was added potassium carbonate powder (16.2 g, 116.4 mmol) followed by 2-bromoethanol-$d_4$ (10 g, 77.6 mmol). The reaction was stirred at reflux for 24 h followed by the second addition of 2-bromoethanol-$d_4$ (10 g, 77.6 mmol) and potassium carbonate (16.2 g, 116.4 mmol). The reaction was stirred at reflux until no 1-Boc-piperazine was detected by $^1$H-NMR (approximately 24 h). The reaction mixture was filtered, washed with THF, and concentrated in vacuo to give a crude oil. The crude oil (approximately 77.6 mmol) was dissolved in THF (200 mL), triethylamine (21.8 mL, 155.2 mmol) was added, and the solution was cooled to 0° C. Chlorotrimethylsilane (19.2 mL, 155.2 mmol) was added dropwise and the reaction mixture was stirred overnight at rt, then slowly quenched by the addition of water at 0° C. The resulting mixture was extracted with ethyl acetate (3×200 mL) and the combined organic layers were dried over sodium sulfate then concentrated in vacuo. The resulting crude oil was purified on a silica gel column with 1:1 MTBE/heptane and MTBE as eluent to give 28 as a pale yellow oil (24.5 g).

Synthesis of 1-(1,1,2,2-$d_4$-2-hydroxyethyl)piperazine dihydrochloride (45-$d_4$). To a solution of 28 (24.5 g) in methanol (50 mL) was added with 4.0 M hydrogen chloride in 1,4-dioxane (250 mL). The reaction mixture was stirred for 2 h then concentrated in vacuo to give 45-$d_4$ as a white solid.

Example 3b

Synthesis of 1-(2,2-$d_2$-2-Hydroxyethyl)piperazine dihydrochloride (45-$d_2$)

Intermediate 45-$d_2$ was prepared as outlined in Scheme 3b below. Details of the synthesis are as follows.

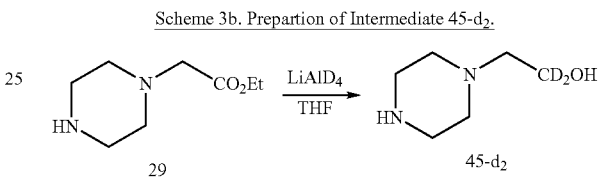

Scheme 3b. Prepartion of Intermediate 45-$d_2$.

Synthesis of 1-(2,2-$d_2$-2-hydroxyethyl)piperazine dihydrochloride (45-$d_2$). To a solution of ethyl piperazine-1-acetate 29 (25 g, 145.2 mmol) in THF (400 mL) at 0° C. was added lithium aluminum deuteride (6.09 g, 145.2 mmol) in portions. The reaction was stirred overnight at rt, cooled to 0° C., then slowly quenched by the addition of water (6 mL), 15 wt % NaOH (6 mL), and water (6 mL) sequentially. The mixture was filtered over Celite, and washed with THF (200 mL). The filtrate was concentrated in vacuo to give 45-$d_2$ as a pale yellow oil in quantitative yield.

Example 3c

Synthesis of 1-(2-Hydroxyethyl)-2,2,3,3,5,5,6,6-$d_8$-piperazine dihydrochloride (45-$d_8$)

Intermediate 45-$d_8$ was prepared as outlined in Scheme 3c below. Details of the synthesis are set forth below.

Scheme 3c. Prepartion of Intermediates 45-$d_8$ and 45-$d_{12}$.

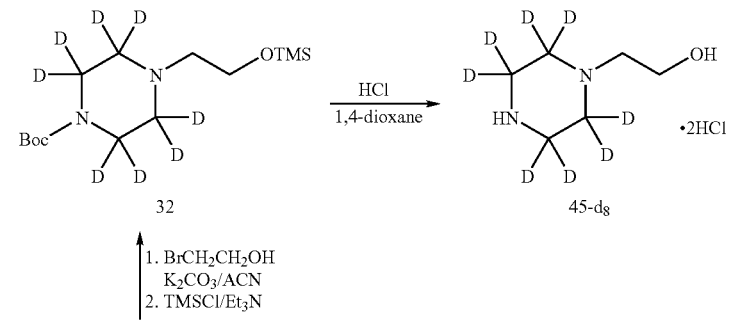

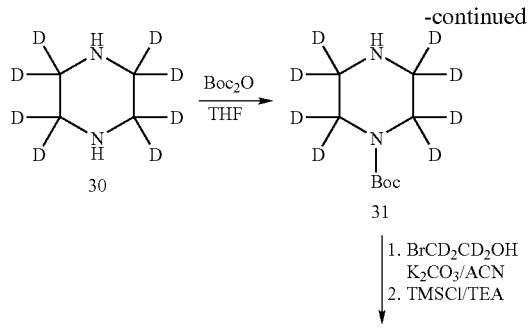

-continued

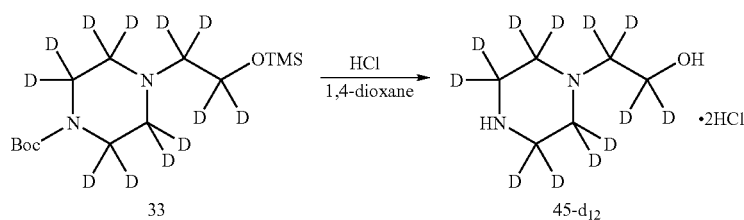

Synthesis of tert-butyl 2,2,3,3,5,5,6,6-d$_8$-piperazine-1-carboxylate (31). To a suspension of 2,2,3,3,5,5,6,6-d$_8$-piperazine dihydrochloride 30 (19 g, 113.6 mmol) in methanol (300 mL) was added sodium hydroxide (4.8 g, 120.0 mmol). The suspension was stirred at reflux for 3 h, cooled to rt, filtered, then washed with methanol (100 mL). The filtrate was rid of solvent in vacuo, then dissolved in water (120 mL) and t-BuOH (137 mL), followed by the addition of 2.5 N NaOH (114 mL, 284 mmol). The resulting solution was cooled to 0° C. and a solution of di-tert-butyl dicarbonate (12.4 g, 56.8 mmol) in t-BuOH was added over a period of 2 h. The reaction mixture was stirred overnight at rt. t-BuOH was removed under vacuum and the precipitate (1,4-bis-Boc-piperazine) was filtered and washed with a small amount of water. The filtrate was extracted with CH$_2$Cl$_2$ (4×200 mL) and the extracts were dried over sodium sulfate and concentrated in vacuo to give 31 as semi-solid (8.37 g, 76%).

Synthesis of tert-butyl 4-(2-(trimethylsilyloxy)-ethyl)-2,2,3,3,5,5,6,6-d$_8$-piperazine-1-carboxylate (32). To a solution of 1-Boc-2,2,3,3,5,5,6,6-d$_8$-piperazine 31 (6.0 g, 30.9 mmol) in anhydrous acetonitrile (100 mL) was added potassium carbonate powder (12.8 g, 92.7 mmol) followed by 2-bromoethanol (5.8 g, 46.4 mmol). The reaction was stirred under reflux conditions for 24 h followed by the second addition of 2-bromoethanol (5.8 g, 46.4 mmol) and potassium carbonate (12.8 g, 92.7 mmol). The resulting mixture was stirred under reflux conditions for 24 h and was cooled to 0° C. before the addition of triethylamine (26 mL, 185.6 mmol). To this suspension at 0° C., chlorotrimethylsilane (17.6 mL, 139.2 mmol) was added dropwise. The reaction mixture was stirred overnight at rt, filtered, and washed with THF (200 mL). The filtrate was concentrated in vacuo and the crude oil was purified on a silica gel column with 1:1 MTBE/heptane and MTBE as eluent to give 32 as a pale yellow oil (5.97 g, 62%).

Synthesis of 1-(2-hydroxyethyl)-2,2,3,3,5,5,6,6-d$_8$-piperazine dihydrochloride (45-d$_8$). To a solution of 32 (5.97 g) in methanol (30 mL) was added with 4.0 M hydrogen chloride in 1,4-dioxane (100 mL). The reaction mixture was stirred for 2 h then concentrated in vacuo to give 45-d$_8$ as a white solid in quantitative yield.

Example 3d

Synthesis of 1-(1,1,2,2-d$_4$-2-Hydroxyethyl)-2,2,3,3,5,5,6,6-d$_8$-piperazine dihydrochloride (45-d$_{12}$)

Intermediate 45-d$_{12}$ was prepared as outlined in Scheme 3c above. Details of the synthesis are set forth below.

Synthesis of tert-butyl-4-(2-(trimethylsilyloxy)-1,1,2,2-d$_4$-ethyl)-2,2,3,3,5,5,6,6-d$_8$-piperazine-1-carboxylate (33). To a solution of 1-Boc-2,2,3,3,5,5,6,6-d$_8$-piperazine 31 (3.4 g, 17.5 mmol) in anhydrous acetonitrile (60 mL) was added potassium carbonate powder (7.3 g, 52.5 mmol) followed by 2-bromoethanol-d$_4$ (5.0 g, 38.8 mmol). The reaction was stirred under reflux conditions for 48 h then cooled to 0° C., followed by the addition of triethylamine (5.4 mL, 38.8 mmol). To this suspension at 0° C., chlorotrimethylsilane (4.9 mL, 38.8 mmol) was added dropwise. The reaction mixture was stirred overnight at rt, filtered, and washed with THF (200 mL). The filtrate was concentrated in vacuo and the crude oil was purified on a silica gel column with 1:1 MTBE/heptane and MTBE as eluent to give 33 as a pale yellow oil (3.1 g).

Synthesis of 1-(1,1,2,2-d$_4$-2-hydroxyethyl)-2,2,3,3,5,5,6,6-d$_8$-piperazine dihydrochloride (45-d$_{12}$). To a solution of 33 (3.1 g) in methanol (20 mL) was added with 4.0 M hydrogen chloride in 1,4-dioxane (100 mL). The reaction mixture was stirred for 2 h then concentrated in vacuo to give 45-d$_{12}$ as a white solid in quantitative yield.

Example 4

Synthesis of N-(2-Chloro-6-methylphenyl)-2-(6-(4-(1,1,2,2-d$_4$-2-hydroxyethyl)piperazin-1-yl)-2-methylpyrimidin-4-ylamino)thiazole-5-carboxamide (100)

Compound 100 was prepared as outlined in Scheme 4 below. Details of the synthesis are set forth as General Procedure A below.

Scheme 4. Preparation of Compound 100.

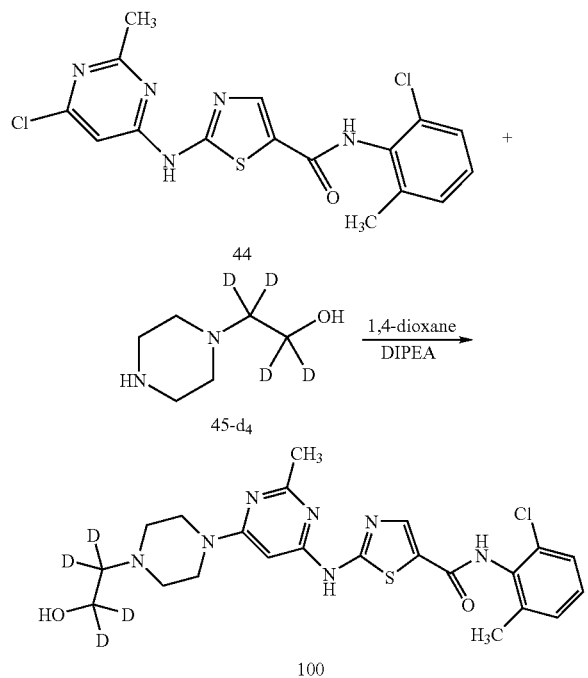

General Procedure A. To a suspension of thiazole-carboxamide 44 (1.0 eq, prepared as outlined in McIntyre, J A et al., Drugs of the Future, 2006, 31(4): 291) in 1,4-dioxane (10 mL/1 mmol) at rt was added diisopropylethylamine (DIPEA, 5.0 eq) followed by the piperazine 45-d$_4$ (1.5 eq to 5.0 eq; generally 1.5 eq of the piperazine analogue was enough to achieve the complete displacement with extended reaction time). The reaction mixture was stirred under reflux conditions until no starting material was detectable (24-72 h), was stripped of solvent in vacuo, then dry-loaded onto a silica-gel column with 94:5:1 CH$_2$Cl$_2$/MeOH/ammonium hydroxide as eluent to give the desired product in 96 to >99% purity. Occasionally, residual solvents, detected by $^1$H-NMR, were removed by co-evaporation with water.

Compound 100: $^1$H-NMR (300 MHz, DMSO-d$_6$): δ 2.24 (s, 3H), 2.41 (s, 3H), 2.48-2.51 (m, 4H, obscured by DMSO peak), 3.51 (bs, 4H), 4.42 (s, 1H), 6.05 (s, 1H), 7.23-7.31 (m, 2H), 7.41 (dd, J$_1$=7.3, J$_2$=2.0, 1H), 8.22 (s, 1H), 9.90 (s, 1H), 11.50 (s, 1H). $^{13}$C-NMR (75 MHz, DMSO-d$_6$): δ 18.20, 25.49, 43.48, 52.57, 82.48, 125.57, 126.92, 128.08, 128.94, 132.32, 133.40, 138.71, 140.71, 156.80, 159.80, 162.26, 162.44, 165.05. HPLC (method: 20 mm C18-RP column—gradient method 2-95% ACN+0.1% formic acid in 3.3 min with 1.7 min hold at 95% ACN; Wavelength: 254 nm): retention time: 2.57 min. MS (M+H): 492.0. Elemental Analysis (C$_{22}$H$_{22}$D$_4$ClN$_7$O$_2$S.0.25H$_2$O): Calculated: C=53.22; H=5.38; Cl=7.14; N=19.75; S=6.46. Found: C=53.22; H=5.27; Cl=7.48; N=19.51; S=6.60.

Example 5

Synthesis of N-(2-Chloro-6-methylphenyl)-2-(6-(4-(2,2-d$_2$-2-hydroxyethyl)piperazin-1-yl)-2-methylpyrimidin-4-ylamino)thiazole-5-carboxamide (116)

Compound 116 was prepared as generally outlined in Scheme 4 above using appropriately deuterated reagents. Details of the synthesis are set forth as General Procedure A above, replacing 45-d$_4$ with 45-d$_2$ (see Example 3b).

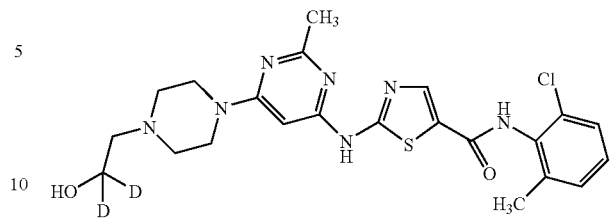

Compound 116: $^1$H-NMR (300 MHz, DMSO-d$_6$): δ 2.24 (s, 3H), 2.41 (s, 3H), 2.50-2.51 (m, 6H, obscured by DMSO peak), 3.51 (bs, 4H), 4.44 (bs, 1H), 6.05 (s, 1H), 7.23-7.31 (m, 2H), 7.40 (dd, J$_1$=7.3, J$_2$=2.0, 1H), 8.22 (s, 1H), 9.90 (s, 1H), 11.49 (s, 1H). $^{13}$C-NMR (75 MHz, DMSO-d$_6$): δ 18.99, 26.27, 44.24, 53.39, 60.71, 83.27, 126.37, 127.70, 128.88, 129.72, 133.10, 134.18, 139.50, 141.49, 157.60, 160.59, 163.05, 163.23, 165.85. HPLC (method: 20 mm C18-RP column—gradient method 2-95% ACN+0.1% formic acid in 3.3 min with 1.7 min hold at 95% ACN; Wavelength: 254 nm): retention time: 2.57 min. MS (M+H): 490.2. Elemental Analysis (C$_{22}$H$_{24}$D$_2$ClN$_7$O$_2$S.0.25H$_2$O): Calculated: C=53.43; H=5.40; Cl=7.17; N=19.83; S=6.48. Found: C=53.39; H=5.38; Cl=7.56; N=19.36; S=6.35.

Example 6

Synthesis of N-(2-Chloro-6-methylphenyl)-2-(6-(4-(2-hydroxyethyl)-(piperazin-d$_8$)-1-yl)-2-methylpyrimidin-4-ylamino)thiazole-5-carboxamide (117)

Compound 117 was prepared as generally outlined in Scheme 4 above using appropriately deuterated reagents. Details of the synthesis are set forth as General Procedure A above, replacing 45-d$_4$ with 45-d$_8$ (see Example 3c).

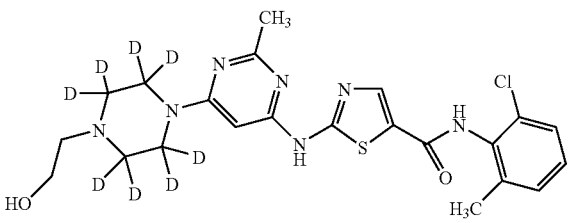

Compound 117: $^1$H-NMR (300 MHz, DMSO-d$_6$): δ 2.24 (s, 3H), 2.40 (s, 3H), 2.41-2.43 (m, 2H), 3.53-3.55 (m, 2H), 4.42-4.50 (m, 1H), 6.03 (s, 1H), 7.23-7.29 (m, 2H), 7.39-7.41 (m, 1H), 8.22 (s, 1H), 9.89 (s, 1H), 11.49 (s, 1H). $^{13}$C-NMR (75 MHz, DMSO-d$_6$): δ 18.99, 26.27, 59.19, 60.80, 83.23, 126.36, 127.70, 128.88, 129.72, 133.10, 134.18, 139.50, 141.50, 157.58, 160.59, 163.08, 163.23, 165.85. HPLC (method: 20 mm C18-RP column—gradient method 2-95% ACN+0.1% formic acid in 3.3 min with 1.7 min hold at 95% ACN; Wavelength: 254 nm): retention time: 2.58 min. MS (M+H): 496.2. Elemental Analysis (C$_{22}$H$_{18}$D$_8$ClN$_7$O$_2$S.⅓H$_2$O): Calculated: C=52.63; H=5.35; N=19.53; S=6.39. Found: C=52.62; H=4.97; N=19.17; S=6.51.

Example 7

Synthesis of N-(2-Chloro-6-(methyl-d$_3$)phenyl)-2-(6-(4-(2-hydroxyethyl)piperazin-1-yl)-2-methylpyrimidin-4-ylamino)thiazole-5-carboxamide (118)

Compound 118 was prepared as generally outlined in Scheme 4 above using appropriately deuterated reagents. Details of the synthesis are set forth as General Procedure A above, replacing 44 with 44-d$_3$ (see Example 2) and replacing 45-d$_4$ with 45 (commercially available).

118

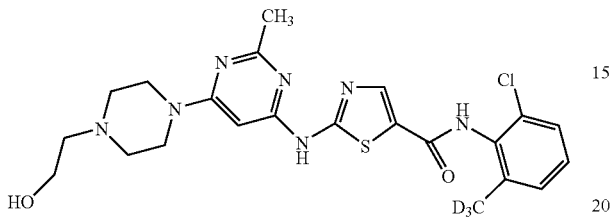

Compound 118: $^1$H-NMR (300 MHz, DMSO-d$_6$): δ 2.41 (s, 3H), 2.43-2.51 (m, 6H, obscured by DMSO peak), 3.51-3.56 (m, 6H), 4.50 (bs, 1H), 6.05 (s, 1H), 7.23-7.31 (m, 2H), 7.41 (dd, J$_1$=7.3, J$_2$=2.3, 1H), 8.22 (s, 1H), 9.90 (s, 1H), 11.51 (s, 1H). $^{13}$C-NMR (75 MHz, DMSO-d$_6$): δ 26.27, 44.22, 53.38, 59.14, 60.84, 83.27, 126.37, 127.71, 128.88, 129.71, 133.08, 134.21, 139.39, 141.40, 157.59, 160.59, 163.04, 163.21, 165.85. HPLC (method: 20 mm C18-RP column—gradient method 2-95% ACN+0.1% formic acid in 3.3 min with 1.7 min hold at 95% ACN; Wavelength: 254 nm): retention time: 2.57 min. MS (M+H): 491.1. Elemental Analysis (C$_{22}$H$_{23}$D$_3$ClN$_7$O$_2$S.0.5H$_2$O): Calculated: C=52.85; H=5.44; Cl=7.09; N=19.61; S=6.41. Found: C=53.16; H=5.25; Cl=6.95; N=19.45; S=6.68.

Example 8

Synthesis of N-(2-Chloro-6-(methyl-d$_3$)phenyl)-2-(6-(4-(1,1,2,2-d$_4$-2-hydroxyethyl)piperazin-1-yl)-2-methylpyrimidin-4-ylamino)thiazole-5-carboxamide (103)

Compound 103 was prepared as generally outlined in Scheme 4 above using appropriately deuterated reagents. Details of the synthesis are set forth as General Procedure A above, replacing 44 with 44-d$_3$ (see Example 2).

103

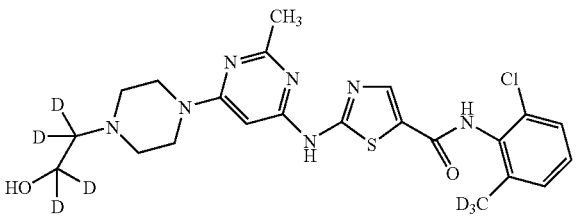

Compound 103: $^1$H-NMR (300 MHz, DMSO-d$_6$): δ 2.41 (s, 3H), 2.48-2.51 (m, 4H, obscured by DMSO peak), 3.51 (bs, 4H), 4.42 (s, 1H), 6.04 (s, 1H), 7.26-7.31 (m, 2H), 7.41 (dd, J$_1$=7.3, J$_2$=2.3, 1H), 8.22 (s, 1H), 9.89 (s, 1H), 11.50 (s, 1H). $^{13}$C-NMR (75 MHz, DMSO-d$_6$): δ 25.49, 43.48, 52.57, 82.47, 125.57, 126.92, 128.09, 128.93, 132.30, 133.42, 138.60, 140.71, 156.80, 159.80, 162.26, 162.44, 165.05. HPLC (method: 20 mm C18-RP column—gradient method 2-95% ACN+0.1% formic acid in 3.3 min with 1.7 min hold at 95% ACN; Wavelength: 254 nm): retention time: 2.59 min. MS (M+H): 495.0. Elemental Analysis (C$_{22}$H$_{19}$D$_7$ClN$_7$O$_2$S.0.25H$_2$O): Calculated: C=52.89; H=5.35; Cl=7.10; N=19.63; S=6.42. Found: C=53.00; H=5.25; Cl=7.40; N=19.36; S=6.37.

Example 9

Synthesis of N-(2-Chloro-6-(methyl-d$_3$)phenyl)-2-(6-(4-(2,2-d$_2$-2-hydroxyethyl)piperazin-1-yl)-2-methylpyrimidin-4-ylamino)thiazole-5-carboxamide (101)

Compound 101 was prepared as generally outlined in Scheme 4 above using appropriately deuterated reagents. Details of the synthesis are set forth as General Procedure A above, replacing 44 with 44-d$_3$ (see Example 2) and replacing 45-d$_4$ with 45-d$_2$ (see Example 3b).

101

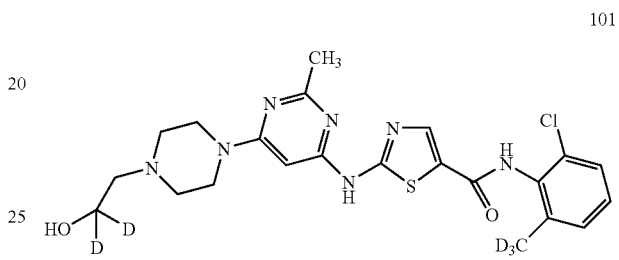

Compound 101: $^1$H-NMR (300 MHz, DMSO-d$_6$): δ 2.41 (s, 3H), 2.48-2.50 (m, 6H, obscured by DMSO peak), 3.51 (bs, 4H), 4.43 (s, 1H), 6.05 (s, 1H), 7.26-7.28 (m, 2H), 7.40 (dd, J$_1$=7.3, J$_2$=2.3, 1H), 8.22 (s, 1H), 9.90 (s, 1H), 11.49 (s, 1H). $^{13}$C-NMR (75 MHz, DMSO-d$_6$): δ 26.27, 44.26, 53.42, 60.74, 83.26, 126.37, 127.71, 128.87, 129.71, 133.08, 134.21, 139.40, 141.50, 157.60, 160.60, 163.05, 163.23, 165.84. HPLC (method: 20 mm C18-RP column—gradient method 2-95% ACN+0.1% formic acid in 3.3 min with 1.7 min hold at 95% ACN; Wavelength: 254 nm): retention time: 2.56 min. MS (M+H): 493.2. Elemental Analysis (C$_{22}$H$_{21}$D$_5$ClN$_7$O$_2$S.0.5H$_2$O): Calculated: C=52.63; H=5.42; Cl=7.06; N=19.53; S=6.39. Found: C=52.49; H=5.18; Cl=7.43; N=19.18; S=6.38.

Example 10

Synthesis of N-(2-Chloro-6-(methyl-d$_3$)phenyl)-2-(6-(4-(2-hydroxyethyl)-(piperazin-d$_8$)-1-yl)-2-methylpyrimidin-4-ylamino)thiazole-5-carboxamide (119)

Compound 119 was prepared as generally outlined in Scheme 4 above using appropriately deuterated reagents. Details of the synthesis are set forth as General Procedure A above, replacing 44 with 44-d$_3$ (see Example 2) and replacing 45-d$_4$ with 45-d$_8$ (see Example 3c).

119

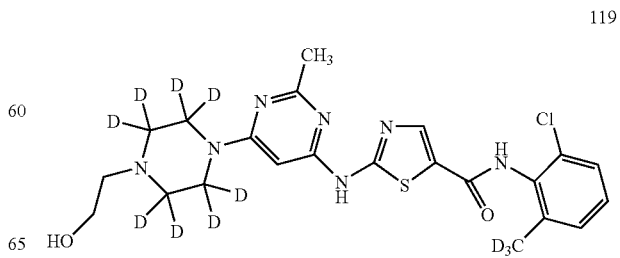

Compound 119: $^1$H-NMR (300 MHz, DMSO-$d_6$): δ 2.38 (s, 3H), 3.32-3.36 (m, 2H, obscured by H$_2$O peak), 3.45-3.52 (m, 2H), 4.40-4.60 (m, 1H), 6.03 (s, 1H), 7.20-7.27 (m, 2H), 7.37 (dd, $J_1$=7.0, $J_2$=2.3, 1H), 8.21 (s, 1H), 9.89 (s, 1H), 11.48 (s, 1H). $^{13}$C-NMR (75 MHz, DMSO-$d_6$): δ 26.25, 58.72, 60.48, 83.29, 126.37, 127.70, 128.87, 129.70, 133.06, 134.18, 139.37, 141.49, 157.58, 160.59, 163.01, 163.18, 165.86. HPLC (method: 20 mm C18-RP column—gradient method 2-95% ACN+0.1% formic acid in 3.3 min with 1.7 min hold at 95% ACN; Wavelength: 254 nm): retention time: 2.55 min. MS (M+H): 499.2. Elemental Analysis ($C_{22}H_{15}D_{11}ClN_7O_2S \cdot 2H_2O$): Calculated: C=49.39; H=5.65; N=18.33. Found: C=49.73; H=5.76; N=18.73.

Example 11

Synthesis of N-(2-Chloro-6-(methyl-$d_3$)phenyl)-2-(6-(4-(1,1,2,2-$d_4$-2-hydroxyethyl)-(piperazin-$d_8$)-1-yl)-2-methylpyrimidin-4-ylamino)thiazole-5-carboxamide (115)

Compound 115 was prepared as generally outlined in Scheme 4 above using appropriately deuterated reagents. Details of the synthesis are set forth as General Procedure A above, replacing 44 with 44-$d_3$ (see Example 2) and replacing 45-$d_4$ with 45-$d_{12}$ (see Example 3d).

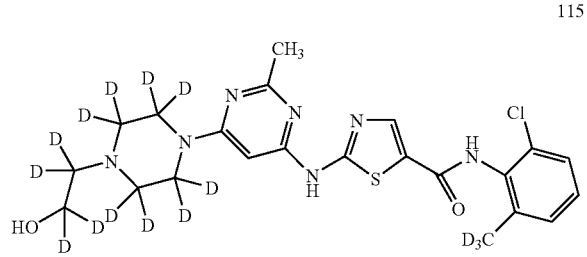

115

Compound 115: $^1$H-NMR (300 MHz, DMSO-$d_6$): δ 2.37 (s, 3H), 4.40 (s, 1H), 6.00 (s, 1H), 7.19-7.26 (m, 2H), 7.37 (dd, $J_1$=7.3, $J_2$=2.3, 1H), 8.19 (s, 1H), 9.86 (s, 1H), 11.46 (s, 1H). $^{13}$C-NMR (75 MHz, DMSO-$d_6$): δ 26.26, 83.21, 126.31, 127.70, 128.87, 129.71, 133.07, 134.19, 139.39, 141.51, 157.56, 160.58, 163.05, 165.84. HPLC (method: 20 mm C18-RP column—gradient method 2-95% ACN+0.1% formic acid in 3.3 min with 1.7 min hold at 95% ACN; Wavelength: 254 nm): retention time: 2.58 min. MS (M+H): 503.1. Elemental Analysis ($C_{22}H_{11}D_{15}ClN_7O_2S \cdot 1.4H_2O$): Calculated: C=50.02; H=5.50; Cl=6.71; N=18.56; S=6.072. Found: C=50.32; H=5.35; Cl=6.45; N=17.98; S=5.72.

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay: Human liver microsomes (20 mg/mL) were obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) were purchased from Sigma-Aldrich. The incubation mixtures were prepared according to Table 2:

TABLE 2

Reaction Mixture Composition for Human Liver Microsome Study

| Liver Microsomes | 0.5 mg/mL |
|---|---|
| Potassium Phosphate, pH 7.4 | 100 mM |
| Magnesium Chloride | 3 mM |

Determination of Metabolic Stability: Two aliquots of this reaction mixture were used for a compound of this invention. The aliquots were incubated in a shaking water bath at 37° C. for 3 minutes. The test compound was then added into each aliquot at a final concentration of 0.5 μM. The reaction was initiated by the addition of cofactor (NADPH) into one aliquot (the other aliquot lacking NADPH served as the negative control). Both aliquots were then incubated in a shaking water bath at 37° C. Fifty microliters (50 μL) of the incubation mixtures were withdrawn in triplicate from each aliquot at 0, 5, 10, 20, and 30 minutes and combined with 50 μL of ice-cold acetonitrile to terminate the reaction. The same procedure was followed for dasatinib and for the positive control, 7-ethoxycoumarin. Testing was done in triplicate.

Data analysis: The in vitro half-lives ($t_{1/2}$s) for test compounds were calculated from the slopes of the linear regression of % parent remaining (ln) vs incubation time relationship.

in vitro $t_{1/2}=0.693/k$ k=−[slope of linear regression of % parent remaining(ln) vs incubation time]

Data analysis was performed using Microsoft Excel Software.

The metabolic stability of compounds of Formula I was tested using pooled liver microsomal incubations. Full scan LC-MS analysis was then performed to detect major metabolites. Samples of the test compounds, exposed to pooled human liver microsomes, were analyzed using HPLC-MS (or MS/MS) detection. For determining metabolic stability, multiple reaction monitoring (MRM) was used to measure the disappearance of the test compounds. For metabolite detection, Q1 full scans were used as survey scans to detect the major metabolites.

The data is summarized in Table 3 and FIG. 1 and shows that compounds 101, 103, 115 and 117 had 16-25% longer half lives in the HLM assay than dasatinib.

TABLE 3

HLM Stability Data for Compounds 101, 103, 115 and 117 Compared to Dasatinib

| | $t_{1/2}$ (min) | | |
|---|---|---|---|
| Compound No. | Experiment 1 | Experiment 2 | Average |
| Dasatinib | 16.0 | 14.6 | 15.3 |
| 117 | 19.6 | 18.5 | 19.1 |
| 103 | 19.4 | 17.2 | 18.3 |
| 101 | 17.7 | 18.0 | 17.9 |
| 115 | 17.3 | 18.2 | 17.8 |

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the

I claim:
1. A compound of Formula I:

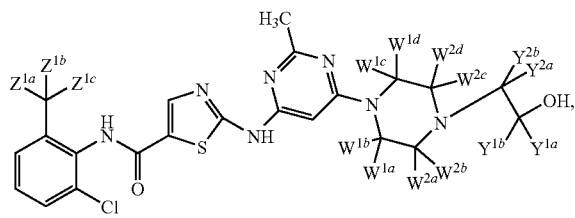

Formula I or a salt thereof; wherein:
each W is independently selected from hydrogen or deuterium;
each Y is independently selected from hydrogen or deuterium;
each Z is independently selected from hydrogen or deuterium; and at least one W, Y, or Z is deuterium, wherein the compound is selected from the group consisting of the compounds defined in the table below:

| Cmpd | Each $Y^1$ | Each $Y^2$ | Each Z | Each $W^1$ | Each $W^2$ |
|------|------------|------------|--------|------------|------------|
| 101  | D | H | D | H | H |
| 103  | D | D | D | H | H |
| 115  | D | D | D | D | D | wherein any atom not designated as deuterium is present at its natural isotopic abundance.

2. A pyrogen-free pharmaceutical composition comprising a compound of claim 1 and an acceptable carrier.

3. A method of treating leukemia in a subject in need thereof, comprising administering to the subject a composition of claim 2.

4. The method of claim 3, wherein the leukemia is chronic myeloid leukemia or acute lymphoblastic leukemia.

* * * * *